(12) United States Patent
Schipper et al.

(10) Patent No.: US 11,632,974 B2
(45) Date of Patent: Apr. 25, 2023

(54) NUTRITIONAL COMPOSITION FOR IMPROVING CELL MEMBRANES

(71) Applicant: N.V. Nutricia, Zoetermeer (NL)

(72) Inventors: Anniek Lidewij Schipper, Utrecht (NL); Eline Marleen Van Der Beek, Utrecht (NL); Dennis Stanley Acton, Utrecht (NL); Nana Bartke, Utrecht (NL); Stefanie Schoen, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 992 days.

(21) Appl. No.: 16/435,141

(22) Filed: Jun. 7, 2019

(65) Prior Publication Data

US 2019/0289893 A1 Sep. 26, 2019

Related U.S. Application Data

(63) Continuation of application No. PCT/EP2017/081998, filed on Dec. 8, 2017.

(30) Foreign Application Priority Data

Dec. 9, 2016 (EP) .................................... 16203280
Mar. 30, 2017 (EP) .................................... 17163858

(51) Int. Cl.

| A23L 33/12 | (2016.01) |
|---|---|
| A23L 33/105 | (2016.01) |
| A23L 33/21 | (2016.01) |
| A23L 33/00 | (2016.01) |
| A23L 33/115 | (2016.01) |
| A61K 31/202 | (2006.01) |
| A23D 9/013 | (2006.01) |
| A61K 31/201 | (2006.01) |
| A61K 31/20 | (2006.01) |
| A61K 31/683 | (2006.01) |
| A61P 25/28 | (2006.01) |

(52) U.S. Cl.
CPC .............. *A23L 33/12* (2016.08); *A23D 9/013* (2013.01); *A23L 33/105* (2016.08); *A23L 33/115* (2016.08); *A23L 33/21* (2016.08); *A23L 33/40* (2016.08); *A61K 31/20* (2013.01); *A61K 31/201* (2013.01); *A61K 31/202* (2013.01); *A61K 31/683* (2013.01); *A23V 2002/00* (2013.01); *A23V 2200/322* (2013.01); *A23V 2250/1868* (2013.01); *A23V 2250/1872* (2013.01); *A23V 2250/1876* (2013.01); *A23V 2250/194* (2013.01); *A23V 2250/284* (2013.01); *A61P 25/28* (2018.01)

(58) Field of Classification Search
None
See application file for complete search history.

(56) References Cited

U.S. PATENT DOCUMENTS

| 5,709,888 | A | 1/1998 | Gil et al. |
|---|---|---|---|
| 7,776,332 | B1 | 8/2010 | Kuslys et al. |
| 8,883,219 | B2 | 11/2014 | Van Der Beek et al. |
| 9,320,294 | B2 | 4/2016 | Van Baalen et al. |
| 9,345,259 | B2 | 5/2016 | Van Der Beek et al. |
| 9,532,966 | B2 | 1/2017 | Van Der Beek et al. |
| 9,649,286 | B2 | 5/2017 | Van Der Beek et al. |
| 2002/0004527 | A1 | 1/2002 | Auestad et al. |
| 2003/0104078 | A1 | 6/2003 | Barrett-Reis et al. |
| 2004/0022922 | A1 | 2/2004 | Rutenberg |
| 2004/0062820 | A1 | 4/2004 | Lasekan et al. |
| 2005/0037089 | A1 | 2/2005 | Jobbins |
| 2005/0214392 | A1 | 9/2005 | McPeak et al. |
| 2006/0188614 | A1 | 8/2006 | Shapira |
| 2006/0210697 | A1 | 9/2006 | Mower |
| 2007/0073193 | A1 | 3/2007 | Park |
| 2007/0073194 | A1 | 3/2007 | Chen et al. |
| 2008/0003330 | A1 | 1/2008 | Rueda et al. |
| 2008/0064656 | A1 | 3/2008 | Van Tol |
| 2008/0292724 | A1 | 11/2008 | Hageman et al. |
| 2009/0011075 | A1 | 1/2009 | Shulman et al. |
| 2009/0136615 | A1 | 5/2009 | Speelmans et al. |
| 2009/0186803 | A1 | 7/2009 | Zwijsen et al. |
| 2011/0206743 | A1 | 8/2011 | Van Baalen et al. |
| 2011/0217411 | A1 | 9/2011 | Van Der Beek et al. |
| 2011/0294757 | A1 | 12/2011 | Shulman et al. |
| 2011/0300204 | A1 | 12/2011 | Van Der Beek et al. |
| 2011/0300225 | A1 | 12/2011 | Van Der Beek et al. |
| 2012/0035274 | A1 | 2/2012 | Park |
| 2012/0039852 | A1 | 2/2012 | Darimont-Nicolau et al. |

(Continued)

FOREIGN PATENT DOCUMENTS

| EP | 0 333 288 A1 | 9/1989 |
|---|---|---|
| EP | 1 252 824 A2 | 10/2002 |

(Continued)

OTHER PUBLICATIONS

"30 percent of the world is now overweight or obese, no country immune", FOX News, May 29, 2014, retrieved Sep. 21, 2016 from URL: http://www.foxnews.com/health/2014/05/29/30-percent-world-is-now-overweight-or-obese-no-country-immune.html (6 pages).
"Glycosphingolipid", Wikipedia, retrieved Oct. 5, 2015, from URL: https://en.wikipedia.org/wiki/Glycosphingolipid (1 page).
"InFat—the premium choice for infant formula—closer to mother's milk", AAK Magazine, Nov. 2009 (1 page).
"Obesity Prevention Source: Prenatal and Early Life Influences", Harvard University, retrieved Jul. 11, 2016 from URL: https://www.hsph.harvard.edu/obesity-prevention-source/obesity-causes/prenatal-postnatal . . . (11 pages).
"Osteoporosis", PubMed Health, U.S. National Library of Medicine, retrieved Jul. 15, 2012 from URL: http;www.ncbi.nlm.nih.gov/pubmedhealth/PMH0001400 (6 pages).

(Continued)

*Primary Examiner* — Dale R Miller

(74) *Attorney, Agent, or Firm* — N.V. Nederlandsch Octrooibureau

(57) ABSTRACT

An early in life nutritional intervention with a lipid component having both large lipid globules with phospholipids and an increased amount of palmitic acid in the sn-2 position in triglycerides were found to improve the fatty acid composition of cell membranes, in particular brain membranes.

16 Claims, No Drawings

(56) References Cited

U.S. PATENT DOCUMENTS

| | | |
|---|---|---|
| 2012/0148588 A1 | 6/2012 | Knopf et al. |
| 2013/0052297 A1 | 2/2013 | Van De Heijning et al. |
| 2013/0071446 A1 | 3/2013 | Van Der Beek et al. |
| 2013/0096087 A1 | 4/2013 | Van Der Beek et al. |
| 2014/0093554 A1 | 4/2014 | Van Der Beek et al. |
| 2014/0162223 A1 | 6/2014 | Saavedra et al. |
| 2015/0306117 A1 | 10/2015 | Van Der Beek et al. |
| 2016/0015068 A1 | 1/2016 | Ao et al. |
| 2016/0205983 A1 | 7/2016 | Van Baalen et al. |
| 2016/0219915 A1 | 8/2016 | Van Der Beek et al. |

FOREIGN PATENT DOCUMENTS

| | | |
|---|---|---|
| EP | 1 800 675 A1 | 6/2007 |
| EP | 2 305 049 | 4/2011 |
| EP | 2 465 359 | 6/2012 |
| EP | 2 583 562 A1 | 4/2013 |
| EP | 2 825 062 B1 | 1/2015 |
| JP | 2001-158736 | 6/2001 |
| SU | 1084006 A | 4/1984 |
| WO | WO-98/44917 A1 | 10/1998 |
| WO | WO-03/005836 A2 | 1/2003 |
| WO | WO-2005/007373 A1 | 1/2005 |
| WO | WO-2005/051091 A1 | 6/2005 |
| WO | WO-2005/051092 A2 | 6/2005 |
| WO | WO-2005/063050 A1 | 7/2005 |
| WO | WO-2006/052134 A2 | 5/2006 |
| WO | WO-2006/094995 A1 | 9/2006 |
| WO | WO-2006/114790 A2 | 11/2006 |
| WO | WO-2007/039596 A1 | 4/2007 |
| WO | WO-2007/073192 A2 | 6/2007 |
| WO | WO-2007/073193 A2 | 6/2007 |
| WO | WO-2007/073194 A2 | 6/2007 |
| WO | WO-2007/097523 A2 | 8/2007 |
| WO | WO-2008/005033 A1 | 1/2008 |
| WO | WO-2008/054192 A1 | 5/2008 |
| WO | WO-2008/071667 A1 | 6/2008 |
| WO | WO-2008/081934 A1 | 7/2008 |
| WO | WO-2009/051502 A1 | 4/2009 |
| WO | WO-2009/057121 A1 | 5/2009 |
| WO | WO-2009/066685 A1 | 5/2009 |
| WO | WO-2009/138680 A2 | 11/2009 |
| WO | WO-2009/154448 A1 | 12/2009 |
| WO | WO-2010/027258 A1 | 3/2010 |
| WO | WO-2010/027259 A1 | 3/2010 |
| WO | WO-2010/068086 A1 | 6/2010 |
| WO | WO-2010/068103 A1 | 6/2010 |
| WO | WO-2010/068105 A1 | 6/2010 |
| WO | WO-2010/070613 A2 | 6/2010 |
| WO | WO-2010/134810 | 11/2010 |
| WO | WO-2011/071371 A1 | 6/2011 |
| WO | WO-2011/108918 | 9/2011 |
| WO | WO-2011/108934 A1 | 9/2011 |
| WO | WO 2011/115476 A1 | 9/2011 |
| WO | WO-2011/115491 A1 | 9/2011 |
| WO | WO-2011/138457 | 11/2011 |
| WO | WO-2012/173467 A1 | 12/2012 |
| WO | WO-2012/173486 | 12/2012 |
| WO | WO-2013/036102 A1 | 3/2013 |
| WO | WO-2013/036103 A1 | 3/2013 |
| WO | WO-2013/036104 A1 | 3/2013 |
| WO | WO-2013/036123 A | 3/2013 |
| WO | WO-2013/153071 A2 | 10/2013 |
| WO | WO-2013/191533 A1 | 12/2013 |
| WO | WO 2015/014967 A1 | 2/2015 |
| WO | WO-2015/065193 A1 | 5/2015 |
| WO | WO-2015/067325 | 5/2015 |
| WO | WO-2015/078505 A1 | 6/2015 |
| WO | WO-2015/091789 A2 | 6/2015 |
| WO | WO-2016/024864 A1 | 2/2016 |
| WO | WO-2017/064304 A1 | 4/2017 |

OTHER PUBLICATIONS

Agostoni et al., "Enteral Nutrient Supply for Preterm Infants: Commentary From the European Society for Paediatric Gastroenterology, Hepatology, and Nutrition Committee on Nutrition", Journal of Pediatric Gastroenterology and Nutrition, vol. 50, No. 1, Jan. 2010, pp. 85-91 (7 pages).

Agostoni et al., "Polyunsaturated Fatty Acids in Human Milk and Neurological Development In Breastfed Infants", Current Pediatric Reviews, vol. 1, No. 1, 2005, pp. 25-30 (6 pages).

Andres et al., "Body Fat and Bone Mineral Content of Infants Fed Breast Milk, Cow's Milk Formula, or Soy Formula During the First Year of Life", The Journal of Pediatrics, vol. 163, No. 1, 2013, pp. 49-54 (6 pages).

Benoit et al., "Phospholipid species and minor sterols in Frencn human milks", Food Cnemistry, vol. 120, 2010, pp. 684-691 (8 pages).

Butte et al., "Energy Expenditure and Deposition of Breast-Fed and Formula-Fed Infants during Early Infancy", Pediatric Research, vol. 28, No. 6, 1990, pp. 631-640 (10 pages).

Clausen et al., "Overweight and the Metabolic Syndrome in Adult Offspring of Women with Diet-Treated Gestational Diabetes Mellitus or Type 1 Diabetes", J Clin Endocrinol Metab, vol. 94, No. 7, Jul. 2009, pp. 2464-2470 (8 pages).

Database WPI Week 198447, Thomson Scientific, London, GB, May 12, 2008, AN 1984-293720, XP-002505629 (1 page).

Database WPI Week 200937, Thompson Scientific, London, GB, AN 2009-J69887, Apr. 29, 2010, XP002578379 (2 pages).

Dewey et al., "Breast-fed infants are leaner than formula-fed infants at 1 y of age: the DARLING study", American Journal of Clinical Nutrition, vol. 57, 1993, pp. 140-145 (6 pages).

Dewey et al., "Growth of Breast-Fed and Formula-Fed Infants from 0 to 18 Months: The DARLING Study", Pediatrics, vol. 89, No. 6, Jun. 1992, pp. 1035-1041 (9 pages).

Durand et al., "Particle sizes and stability of UHT bovine, cereal and grain milks", Food Hydrocolloids, 2003, vol. 17, pp. 671-678 (8 pages).

Eriksson et al., "Size at birth, childhood growth and obesity in adult life", International Journal of Obesity, vol. 25, 2001, pp. 735-740 (7 pages).

Fave et al., "Physicochemical Properties of Lipids: New Strategies to Manage Fatty Acid Bioavailability", Cellular and Molecular Biology, vol. 50, No. 7, 2004, pp. 815-831 (17 pages).

Gallier et al., "A novel infant milk formula concept: Mimicking the human milk fat globule structure", Colloids and Surfaces B: Biointerfaces, vol. 136, 2015, pp. 329-339 (11 pages).

Hamilton, James A., "Interactions of Triglycerides with Phospholipids; Incorporation into the Bilayer Structure and Formation of Emulsions", Biochemistry, 1989, vol. 28, pp. 2514-2520 (7 pages).

Holman et al., "Deficiency of essential fatty acids and membrane fluidity during pregnancy and lactation", Proceedings of the National Academy of Sciences of the United States Of America, Biochemistry, vol. 88, Jun. 19, 1991, pp. 4835-4839 (5 pages).

Hur et al., "Influence of initial emulsifier type on microstructural changes occurring in emulsified lipids during in vitro digestion", Food Chemistry, vol. 114, 2009, pp. 253-262 (10 pages).

Jensen et al., "Specialty Lipids for Infant Nutrition. I. Milks and Formulas", Journal of Pediatric Gastroenterology and Nutrition, vol. 15, No. 3, 1992, pp. 232-245 (14 pages).

Joscelyne et al., "Food emulsions using membrane emulsification: conditions for producing small droplets", Journal of Food Engineering, 1999, vol. 39, pp. 59-64 (6 pages).

Koletzko et al., "Lower protein in infant formula is associated with lower weight up to age 2 y: a randomized clinical trial", American Journal of Clinical Nutrition, vol. 89, 2009, pp. 1836-1845 (10 pages).

Li et al., "Do infants fed from bottles lack self-regulation of milk intake compared with directly breasted infants", Pediatrics, vol. 125, pp. e1386-e1393.

Llewellyn et al., "Development and factor structure of the Baby Eating Behaviour Questionnaire in the Gemini birth cohort", Appetite, vol. 57, 2011, pp. 388-396 (9 pages).

(56) References Cited

OTHER PUBLICATIONS

Lubetzky et al., "Energy expenditure in human milk- versus formula-fed preterm infants", The Journal of Pediatrics, vol. 143, Issue 6, Dec. 2003, pp. 750-753 (4 pages).

Lucas, Alan, "Long-Term Programming Effects of Early Nutrition—Implications for the Preterm Infant", Journal of Perinatology, vol. 25, 2005, pp. S2-S6 (5 pages).

Makrides et al., "Fatty acid composition of brain, retina, and erythrocytes in breast- and formula-fed infants", American Journal of Clinical Nutrition, vol. 60, No. 2, 1994, pp. 189-194 (6 pages).

Mallan et al., "Confirmatory factor analysis of the Baby Eating Behaviour Questionnaire and associations with infant weight, gender and feeding mode in an Australian sample", Appetite, vol. 82, Nov. 1, 2014, pp. 43-49 (7 pages).

Marmot, et al. "Effect of breast-feeding on plasma cholesterol and weight in young adults", Journal of Epidemiology and Community Health (1980), vol. 34, pp. 164-167.

McClements, David Julian, "Food Emulsions: Principles, Practices, and Techniques", CRC Press, Second Edition, 2005, Section 7.3 (19 pages).

Michalski et al., "Optical Parameters of Milk Fat Globules for Laser Light Scattering Measurements," Lait, vol. 81, No. 6, pp. 787-796, 2001 (10 pages).

Michalski et al., "Size Distribution of Fat Globules in Human Colostrum, Breast Milk, and Infant Formula", Journal of Dairy Science, American Dairy Science Association, vol. 88, 2005, pp. 1927-1940 (14 pages).

Michalski et al., "The Dispersion State of Milk Fat Influences Triglyceride Metabolism in the Rat," European Journal of Nutrition, 44:436-444 (2005).

Michalski et al., "The supramolecular structure of milk fat influences plasma triacylglycerols and fatty acid profile in the rat", European Journal of Nutrition, vol. 45, 2006, pp. 215-224 (10 pages).

Mun et al., "Influence of Interfacial Composition on in Vitro Digestibility of Emulsified Lipids: Potential Mechanism for Chitosan's Ability to Inhibit Fat Digestion", Food Biophysics, vol. 1, 2006, pp. 21-29 (9 pages).

Oddy, WH, "Infant feeding and obesity risk in the child," Breastfeed Rev., vol. 20, No. 2, Jul. 2012, pp. 7-12 (2 pages).

Oken et al., "Gestational weight gain and child adiposity at age 3 years", American Journal of Obstetrics & Gynecology, vol. 196, Apr. 2007, p. 322.e1-322.e8 (8 pages).

Owen, et al. "Infant Feeding and Blood Cholesterol: A Study in Adolescents and a Systematic Review", Pediatrics (2006) vol. 110, pp. 597-608.

Park et al., "Influence of encapsulation of emulsified lipids with chitosan on their in vivo digestibility", Food Chemistry, vol. 104, 2007, pp. 761-767 (7 pages).

Petrowski, Gary E., "Emulsion Stability and Its Relation to Foods," Carnation Research Laboratories, 1976, pp. 309-359 (51 pages).

Rasmussen et al., "The relation of weight, length and ponderal index at birth to body mass index and overweight among 18-year-old males in Sweden", Abstract, European Journal of Epidemiology, vol. 14, Issue 4, Jun. 1998, pp. 373-380 (7 pages).

Ruegg et al., "The Fat Globule Size Distribution in Human Milk", Biochimica et Biophysica Acta, vol. 666, 1981, pp. 7-14 (8 pages).

Schultz et al., "Review: High-Pressure Homogenization as a Process for Emulsion Formation", Chemical Engineering Technology, vol. 27, No. 4, 2004, pp. 361-368 (8 pages).

Simonin et al., "Comparison of the fat content and fat globule size distribution of breast milk from mothers delivering term and preterm", The American Journal of Clinical Nutrition, vol. 40, Oct. 1984, pp. 820-826 (7 pages).

Snitker et al., "Effects of novel capsinoid treatment on fatness and energy metabolism in humans: possible pharmacogenetic implications", American Journal of Clinical Nutrition, vol. 89, 2009, pp. 45-50 (6 pages).

Sprong et al., "Bovine milk fat components inhibit food-borne pathogens", International Dairy Journal, vol. 12, 2002, pp. 209-215 (7 pages).

Sproston, et al., "Enzymatic Modification of Anhydrous Milkfat with n-3 and n-6 Fatty Acids for Potential Use in Infant Formula: Comparison of Methods", Journal of the American Oil Chemists' Society, vol. 93, 2016, pp. 251-265 (15 pages).

Stunkard et al., "Energy intake, not energy output, is a determinant of body size in infants", American Journal of Clinical Nutrition, vol. 69, 1999, pp. 524-530 (7 pages).

Timby et al., "Neurodevelopment, nutrition, and growth until 12 mo of age in infants fed a low-energy, low-protein formula supplemented with bovine milk fat globule membranes: a randomized controlled trial", American Journal of Clinical Nutrition, Feb. 5, 2014 (9 pages).

Vickers et al., "Supplementation with a mixture of complex lipids derived from milk to growing rats results in improvements in parameters related to growth and cognition", Nutrition Research, vol. 29, 2009, pp. 426-435 (10 pages).

Whittlestone et al., "Variations in the Fat Content of Human Milk During Suckling", Ruakura Animal Research Station, Department of Agriculture, 1953, pp. 204-206 (3 pages).

Young et al., "Biological Determinants Linking Infant Weight Gain and Child Obesity: Current Knowledge and Future Directions", Advances in Nutrition, vol. 3, 2012, pp. 675-686 (12 pages).

International Search Report issued in International Patent Application No. PCT/EP2017/081998, dated Feb. 1, 2018.

International Preliminary Report on Patentability issued in International Patent Application No. PCT/EP2017/081998, dated Feb. 20, 2019.

NUTRITIONAL COMPOSITION FOR IMPROVING CELL MEMBRANES

CROSS-REFERENCE TO RELATED APPLICATIONS

This application is a continuation of International Patent Application No. PCT/EP2017/081998, filed Dec. 8, 2017, which claims priority from European Patent Application Nos. 16203280.9, filed Dec. 9, 2016, and 17163858.8, filed Mar. 30, 2017. The contents of these applications are incorporated herein by reference in their entirety.

FIELD OF THE INVENTION

The present invention is in the field of infant nutrition and the effects on brain development.

BACKGROUND OF THE INVENTION

Breast-feeding is the preferred method of feeding infants. However, there are circumstances that make breast-feeding impossible or less desirable. In those cases infant formulae are a good alternative. The composition of modern infant formulae is adapted in such a way that it meets many of the special nutritional requirements of the fast growing and developing infant.

Still it seems that improvements can be made towards the constitution of infant milk formulae. Early nutrition administered during the specific period of infancy when rapid growth and development of the brain occurs, has a programming effect and therefore has long term consequences on the brain function. Breast-fed infants score better on visual and developmental tests than do formula-fed infants and they have an improved neurodevelopment compared to formula fed infants. In particular, the human milk long-chain polyunsaturated fatty acids (LC-PUFA) such as docosahexaenoic acid (DHA) contribute strongly to the development of the brain and cognitive and visual functions. Breast-fed infants have higher DHA concentrations in their brain compared to formula-fed infants. This contributes to the enhanced cognitive development which seems to persist until adulthood. Some recent clinical studies in infants have shown that DHA supplementation can improve cognitive function of formula fed infants. The difference in neurodevelopment between breast- and bottle-fed infants thus has mainly been attributed to the presence of long chain polyunsaturated fatty acids (LC-PUFA) such as docosahexaenoic acid (DHA) and arachidonic acid (ARA) in breast milk. Most current infant milk formulae therefore now also comprise such LC-PUFA. It has also been found that such LC-PUFA are better incorporated into membranes when they are present in the diet in the form of phospholipids instead of triglycerides.

WO 2009/057121 discloses a method for improving, promoting or maintaining the development of brain and retina in an infant comprising administering a composition comprising at least one triglyceride, at least one phospholipid and at least one long chain polyunsaturated fatty acid (LC-PUFA); wherein at least about 1% of the LC-PUFA in the composition is conjugated to said at least one phospholipid.

The role of dairy fat and polar lipids from milk on the effects of brain has gained attention. WO 2009/051502 discloses the use of one or more complex lipids from milk including gangliosides for maintaining or increasing cognitive development in a foetal, infant or child subject.

WO 2009/138680 discloses that the presence of at least 30% dairy fat in conjunction with a vegetable oil in infant nutrition can be used amongst others to increase endogenous DHA accumulation in brain membranes, and ameliorating brain development and cognitive function. WO2008/005033 discloses infant formulae with gangliosides, phospholipids, sialic acid, docosahexaenoic acid and arachidonic acid for accelerating brain development, neural migration and cognitive development in infants. In all cases a direct diet effect was disclosed, and not effects on the longer term. WO 2013/153071 discloses that an infant formula is tested comprising sialic acid, cholesterol, sphingomyelin, and a lower caloric content and lower protein content compared to the control formula. An improved cognitive function was observed in infants at 12 months of age having consumed the experimental formula WO 2011/115476 and WO 2011/115491 disclose infant nutrition with lipid globules coated with phospholipids for use in improving the fatty acid composition of the membrane and of improvement of cognitive or behavioural performance. WO 2016/024864 discloses infant nutrition with lipid globules coated with phospholipids for improving behaviour.

WO 2005/051091 discloses a lipid preparation, to be included in infant formulae as a beneficial ingredient per se and for improving cognitive and vision development in particular, that is organised in a globular microstructure naturally occurring in human milk.

SUMMARY OF THE INVENTION

Using an animal model the inventors found a synergistically improved fatty acid composition of the brain membranes in mice that had consumed early in life a composition comprising both large lipid globules coated with phospholipids and an increased level of palmitic acid at the sn-2 position of triglycerides. Compared to the control, the amount of PUFA, LC-PUFA, and major individual fatty acid components of the brain membranes docosahexaenoic acid (DHA) and arachidonic acid (ARA) were statistically significantly increased. The increase was also higher than can be expected based on intervention with a composition comprising large lipid globules coated with phospholipids alone or with a composition comprising palmitic acid enriched in the sn-2 position of triglycerides alone. This is thus representative for a synergistic improvement of the cell membrane composition, in particular brain membrane composition, and an increased cell membrane fluidity. Such brain membrane structural effects are correlated with and thus indicative of an improved brain function effect, in particular an improvement of cognitive function. In particular it is an indication that such effects persist later in life. In a clinical trial where infants consumed infant formula with both large lipid globules coated with phospholipids and an increased level of palmitic acid at the sn-2 position of triglycerides, an improvement of the fatty acid composition of red blood cell membranes was observed, when compared with the fatty acid composition of red blood cell membranes of infants that consumed a standard infant formula.

DETAILED DESCRIPTION OF THE INVENTION

The present invention thus concerns a method for improving the fatty acid composition of cell membranes in a human subject by administering a nutritional composition comprising lipid in the form of lipid globules to the human subject, wherein
a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm and/or at least 45 vol. % have a diameter of 2-12 μm, and
d. the lipid comprises at least 0.5 wt. % phospholipid based on total lipid, and either wherein the nutritional composition is not human milk or wherein the nutritional composition comprises vegetable lipid.

The present method can also be referred to as a non-medical method for improving the fatty acid composition of cell membranes in a human subject.

For some jurisdictions, the present invention can also be worded as the use of lipid in the manufacture of a nutritional composition for use in improving the fatty acid composition of cell membranes in a human subject, wherein the lipid is in the form of lipid globules, wherein
a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm and/or at least 45 vol. % have a diameter of 2-12 μm, and
d. the lipid comprises at least 0.5 wt. % phospholipid based on total lipid, and either wherein the nutritional composition is not human milk or wherein the nutritional composition comprises vegetable lipid.

For some jurisdictions, the present invention can also be worded as a nutritional composition comprising lipid in the form of lipid globules, wherein
a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm and/or at least 45 vol. % have a diameter of 2-12 μm, and
d. the lipid comprises at least 0.5 wt. % phospholipid based on total lipid, and wherein the nutritional composition is not human milk or wherein the nutritional composition comprises vegetable lipid, for use in improving the fatty acid composition of cell membranes in a human subject.

In one aspect the present invention concerns a method for i) improving cognitive performance and/or improving cognitive development and/or preventing cognitive impairment, ii) improving behavioural performance and/or improving behavioural development, iii) improving visual acuity, and/or iv) improving fine motor skills, in a human subject by administering a nutritional composition comprising lipid in the form of lipid globules to the human subject, wherein
a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm and/or at least 45 vol. % have a diameter of 2-12 μm, and
d. the lipid comprises at least 0.5 wt. % phospholipid based on total lipid, and either wherein the nutritional composition is not human milk or wherein the nutritional composition comprises vegetable lipid.

The present method can also be referred to as a non-medical method for i) improving cognitive performance and/or improving cognitive development and/or preventing cognitive impairment, ii) improving behavioural performance and/or improving behavioural development, iii) improving visual acuity, and/or iv) improving fine motor skills in a human subject, preferably as a non-medical method for improving cognitive performance and/or improving cognitive development and/or preventing cognitive impairment in a human subject.

For some jurisdictions, the present invention can also be worded as the use of lipid in the manufacture of a nutritional composition for use in i) improving cognitive performance and/or improving cognitive development and/or preventing cognitive impairment, ii) improving behavioural performance and/or improving behavioural development, iii) improving visual acuity, and/or iv) improving fine motor skills, in a human subject, wherein the lipid in the form of lipid globules, wherein
a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm and/or at least 45 vol. % have a diameter of 2-12 μm, and
d. the lipid comprises at least 0.5 wt. % phospholipid based on total lipid, and either wherein the nutritional composition is not human milk or wherein the nutritional composition comprises vegetable lipid.

For some jurisdictions, the present invention can also be worded as a nutritional composition comprising lipid in the form of lipid globules, wherein
a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm and/or at least 45 vol. % have a diameter of 2-12 μm, and
d. the lipid comprises at least 0.5 wt. % phospholipid based on total lipid, and wherein the nutritional composition is not human milk or wherein the nutritional composition comprises vegetable lipid, for use in i) improving cognitive performance and/or improving cognitive development and/or preventing cognitive impairment, ii) improving behavioural performance and/or improving behavioural development, iii) improving visual acuity, and/or iv) improving fine motor skills, in a human subject.

In a preferred embodiment, the method or use or nutritional composition for use is for improving cognitive performance and/or improving cognitive development.

In one aspect the present invention concerns a method for prevention and/or treatment of a disorder associated with impaired brain membrane fatty acid composition selected from the group consisting of consisting of attention deficiency, ADHD, autism, dyslexia, depression, bipolar depression, anxiety, schizophrenia, obsessive compulsive disorder, bulimia, abuse of alcohol or drugs, borderline personality disorder, panic disorder, social phobia, cognitive impairment, dementia, Alzheimer's disease and Parkinson's disease in a human subject by administering a nutritional composition comprising lipid in the form of lipid globules to the human subject, wherein
a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm and/or at least 45 vol. % have a diameter of 2-12 μm, and
d. the lipid comprises at least 0.5 wt. % phospholipid based on total lipid, and either wherein the nutritional composition is not human milk or wherein the nutritional composition comprises vegetable lipid.

For some jurisdictions, the present invention can also be worded as the use of lipid in the manufacture of a nutritional composition for prevention and/or treatment of a disorder associated with impaired brain membrane fatty acid composition selected from the group consisting of consisting of attention deficiency, ADHD, autism, dyslexia, depression, bipolar depression, anxiety, schizophrenia, obsessive compulsive disorder, bulimia, abuse of alcohol or drugs, borderline personality disorder, panic disorder, social phobia, cognitive impairment, dementia, Alzheimer's disease and Parkinson's disease in a human subject, wherein the lipid in the form of lipid globules, wherein
a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm and/or at least 45 vol. % have a diameter of 2-12 μm, and
d. the lipid comprises at least 0.5 wt. % phospholipid based on total lipid, and either wherein the nutritional composition is not human milk or wherein the nutritional composition comprises vegetable lipid.

For some jurisdictions, the present invention can also be worded as a nutritional composition comprising lipid in the form of lipid globules, wherein
a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm and/or at least 45 vol. % have a diameter of 2-12 μm, and
d. the lipid comprises at least 0.5 wt. % phospholipid based on total lipid, and wherein the nutritional composition is not human milk or wherein the nutritional composition comprises vegetable lipid, for use in prevention and/or treatment of a disorder associated with impaired brain membrane fatty acid composition selected from the group consisting of consisting of attention deficiency, ADHD, autism, dyslexia, depression, bipolar depression, anxiety, schizophrenia, obsessive compulsive disorder, bulimia, abuse of alcohol or drugs, borderline personality disorder, panic disorder, social phobia, cognitive impairment, dementia, Alzheimer's disease and Parkinson's disease in a human subject.

In a preferred embodiment the disorder associated with impaired brain membrane fatty acid composition is prevention of cognitive impairment.

Lipid

The nutritional composition that is to be administered according to the present method or use comprises lipids. Preferably lipids in the present invention comprise one or more selected from the group consisting of triglycerides, polar lipids (such as phospholipids, cholesterol, glycolipids, sphingomyelin), free fatty acids, monoglycerides and diglycerides.

The lipids provide preferably 30 to 60% of the total calories of the composition. More preferably the present composition comprises lipid providing 35 to 55% of the total calories, even more preferably the present composition comprises lipids providing 40 to 50% of the total calories. When in liquid form, e.g. as a ready-to-feed liquid, the composition preferably comprises 2.1 to 6.5 g lipids per 100 ml, more preferably 3.0 to 4.0 g per 100 ml. Based on dry weight the present composition preferably comprises 10 to 50 wt. %, more preferably 12.5 to 40 wt. % lipids, even more preferably 19 to 30 wt. % lipids.

The lipid of the present invention preferably comprises vegetable lipids. The presence of vegetable lipids advantageously enables an optimal fatty acid profile, high in polyunsaturated fatty acids and/or more reminiscent to human milk fat. Lipids from cow's milk alone, or other domestic mammals, do not provide an optimal fatty acid profile. The amount of essential fatty acids is too low. This less optimal fatty acid profile, such as a large amount of saturated fatty acids, is known to result in increased obesity. Preferably the present composition comprises at least one, preferably at least two lipid sources selected from the group consisting of linseed oil (flaxseed oil), rape seed oil (such as colza oil, low erucic acid rape seed oil and canola oil), sunflower oil, high oleic sunflower oil, safflower oil, high oleic safflower oil, olive oil, coconut oil, palm oil and palm kernel oil. When in liquid form, e.g. as a ready-to-feed liquid, the composition preferably comprises 1.0 to 6.5 g vegetable lipid per 100 ml, more preferably 1.5 to 4.0 g per 100 nil. Based on dry weight the present composition preferably comprises 5 to 50 wt. %, more preferably 6 to 40 wt. % vegetable lipid, even more preferably 10 to 30 wt. %. Preferably the composition comprises 5 to 100 wt. % vegetable lipids based on total lipids, more preferably 5 to 95 wt. %, more preferably 20 to 80 wt. %, even more preferably 25 to 75 wt. %, most preferably 40 to 60 wt. %. It is noted therefore that the present composition also may comprise non-vegetable lipids. Non-vegetable lipids may include milk fat, milk derived lipids as a preferred source of phospholipids, fish, marine and/or microbial oils as source of LC-PUFA.

Palmitic Acid (PA) at Sn-2 Position of Triglyceride

Triglycerides are the major fraction of the lipids in the nutritional composition. Triglycerides comprise a glycerol moiety to which, via ester bonds, three fatty acid residues are attached, which may be the same or different, and which are generally chosen from saturated and unsaturated fatty acids containing 4 to 26 carbon atoms. Such triglycerides may differ in the fatty acid residues that are present and/or may differ in the respective position(s) of the fatty acid residues to the glycerol backbone (e.g. in the sn-1, -2 and/or -3 position). Preferably the composition comprises at least 70 wt. %, more preferably at least 80 wt. %, more preferably at least 85 wt. % triglycerides, even more preferably at least 90 wt. % triglycerides based on total lipids, even more preferably at least 95 wt. % triglycerides based on total lipids.

An improved cell membrane fatty acid composition was observed when the lipid component had an increased amount of palmitic acid (PA) acid located at the sn-2 position in a triglyceride, based on total PA. Lipids that can be used to enhance the amount of PA located at the sn-2 position in triglycerides based on total PA are commercially available—e.g. from Loders Croklaan under the name Betapol™ and/or can be prepared in a manner known per se, for instance as described in EP 0698078 and/or EP 0758846. Another suitable source is InFat™ of Enzymotec. In case these lipids are obtained by trans- or interesterification of vegetable triglycerides, these sources are in the context of the present invention regarded as vegetable lipids.

A preferred source for triglycerides to enhance PA at the sn-2 or beta position in a triglyceride is non-human animal fat, more preferably non-human mammalian milk fat, even more preferably cow's milk fat. Preferably non-human mammalian milk fat, in particular cow's milk fat, is used in the form of anhydrous milk fat or butter oil. Preferably the source of the milk fat is in a homogenous fat phase, such as butter oil or anhydrous milk fat, and not in the form of oil in water emulsion such as cream, since the lipid globules of the present invention can be more easily prepared during the manufacture of the nutritional composition of the present invention when the lipid is added to the aqueous phase as homogenous fat phase, upon which the mixture is homogenized to an emulsion.

Preferably the amount of the source of lipid comprising triglyceride that has an increased amount of palmitic acid residues in the sn-2 position of a triglyceride that is comprised in the lipid of the nutritional composition that is to be administered according to the present method or use, is between 10 and 99.5 wt. %, more preferably between 10 and 80 wt. % based on total lipid, more preferably between 20 and 80 wt. %, more preferably between 20 and 50 wt. %, even more preferably between 25 and 50 wt. % based on total lipid. Such source of lipid is preferably milk fat, more preferably butter oil or anhydrous milk fat. Preferably the nutritional composition comprises milk fat between 5 and 95 wt. %, more preferably between 20 and 80 wt. % based on total lipid, more preferably between 25 and 75 wt. %, even more preferably between 40 and 60 wt. % based on total lipid.

The lipids used according to the present invention are chosen such that the amount of palmitic acid (PA) that is present in the total lipid of the nutritional composition is at least 10 wt. % based on total fatty acid in the total lipid, preferably at least 15 wt. %. Preferably the amount of PA that is present in the lipids is below 30 wt. %, more preferably between 16 and 24 wt. % based on total fatty acids in the total lipid.

The lipids used according to the present invention are chosen such that based on the total PA present in the lipid at least 15 wt. %, preferably at least 20 wt. %, more preferably at least 25 wt. %, more preferably at least 30 wt. % PA is in the sn-2 or beta position in a triglyceride. Preferably the amount of PA in the sn-2 position in a triglyceride is not more than 45 wt. %, preferably not more than 40 wt. % based on total PA.

Fatty Acid Composition

Herein LA refers to linoleic acid and/or acyl chain (18:2 n6); ALA refers to alpha-linolenic acid and/or acyl chain (18:3 n3); SFA relates to saturated fatty acids and/or acyl chains, MUFA relates to mono-unsaturated fatty acid and/or acyl chains, PUFA refers to polyunsaturated fatty acids and/or acyl chains with 2 or more unsaturated bonds; LC-PUFA refers to long chain polyunsaturated fatty acids and/or acyl chains comprising at least 20 carbon atoms in the fatty acyl chain and with 2 or more unsaturated bonds; DHA refers to docosahexaenoic acid and/or acyl chain (22:6, n3); EPA refers to eicosapentaenoic acid and/or acyl chain (20:5 n3); ARA refers to arachidonic acid and/or acyl chain (20:4 n6); DPA refers to docosapentaenoic acid and/or acyl chain (22:5 n3). PA relates to palmitic acid and/or acyl chains (C16:0). Medium chain fatty acids (MCFA) refer to fatty acids and/or acyl chains with a chain length of 6, 8 or 10 carbon atoms. n3 or omega 3 PUFA relates to refers to polyunsaturated fatty acids and/or acyl chains with 2 or more unsaturated bonds and with an unsaturated bond at the third carbon atom from the methyl end of the fatty acyl chain, n6 or omega 6 PUFA relates to refers to polyunsaturated fatty acids and/or acyl chains with 2 or more unsaturated bonds and with an unsaturated bond at the sixth carbon atom from the methyl end of the fatty acyl chain The present nutritional composition preferably comprises LA. LA is an n6 PUFA and the precursor of n6 LC-PUFA and is an essential fatty acid as it cannot be synthesized by the human body. LA preferably is present in a sufficient amount in order to promote a healthy growth and development, yet in an amount as low as possible to prevent negative, competitive, effects on the formation of n3 PUFA and a too high n6/n3 ratio. The nutritional composition therefore preferably comprises less than 25 wt. %, more preferably less than 20 wt. %, more preferably less than 15 wt. % LA based on total fatty acids. The nutritional composition comprises at least 5 wt. % LA based on fatty acids, preferably at least 7.5 wt. %, more preferably at least 10 wt. % based on total fatty acids.

The present nutritional composition preferably comprises ALA. ALA is a n3 PUFA and the precursor of n3 LC-PUFA and is an essential fatty acid as it cannot be synthesized by the human body. Preferably ALA is present in a sufficient amount to promote a healthy growth and development of the infant. The present nutritional composition therefore comprises at least 0.5 wt. %, more preferably at least 1.0 wt. %, more preferably the nutritional composition comprises at least 1.5 wt. %, even more preferably at least 2.0 wt. % ALA based on total fatty acids. Preferably the nutritional composition comprises less than 10 wt. % ALA, more preferably less than 5.0 wt. % based on total fatty acids. The weight ratio LA/ALA should be well balanced in order to ensure an optimal n6/n3 PUFA, n6/n3 LC PUFA and DHA/ARA ratio in the cellular membranes. Therefore, the present nutritional composition comprises a weight ratio of LA/ALA from 3 to 20, more preferably from 5 to 15, more preferably from 5 to 12, more preferably from 5 to 10. Preferably the n6 PUFA/ n3 PUFA weight ratio is from 3 to 20, more preferably from 3 to 15, more preferably from 5 to 12, more preferably from 5 to 10.

Preferably, the present nutritional composition comprises n3 LC-PUFA, such as EPA, DPA and/or DHA, more preferably DHA. DHA is an important component of brain membranes and is needed for optimal functioning of the neurological tissues. As the conversion of ALA to DHA may be less efficient in infants, preferably both ALA and DHA are present in the nutritional composition. Preferably the present nutritional composition comprises at least 0.05 wt. %, preferably at least 0.1 wt. %, more preferably at least 0.2 wt. %, of DHA based on total fatty acids. Preferably the present nutritional composition comprises not more than 2.0, preferably not more than 1.0 wt. %, of DHA based on total fatty acids.

Since ARA is important in infants for optimal functional membranes, especially membranes of neurological tissues, the present nutritional composition preferably comprises ARA. Preferably the present nutritional composition comprises at least 0.05, preferably at least 0.1 wt. %, more preferably at least 0.2 wt. %, of ARA based on total fatty acids. As the group of n6 fatty acids, especially arachidonic acid (ARA) counteracts the group of n3 fatty acids, especially DHA, the present nutritional composition comprises relatively low amounts of ARA. Preferably the present nutritional composition comprises not more than 2.0, preferably not more than 1.0 wt. %, of ARA based on total fatty acids. Preferably the weight ratio between DHA and ARA is between ¼ to 4/1, more preferably between ½ to 2/1, more preferably between 0.67 and 1.5.

An optimal fatty acid composition of the nutritional composition will aid in an optimal fatty acid composition of the cell membranes, further synergistically aided by the presence of an enhanced amount of sn-2 palmitic acid and phospholipids and the lipid being present in large lipid globules.

Lipid Globule Size

According to the present invention, lipid is present in the nutritional composition in the form of lipid globules. When in liquid form these lipid globules are emulsified in the aqueous phase. Alternatively the lipid globules are present in a powder and the powder is suitable for reconstitution with water or another food grade aqueous phase. The lipid globules comprise a core and a surface.

Standard infant formulae or growing up milks have lipid globules with mode diameter below 0.5 µm. It was found that the presence of large lipid globules have an improved effect on the fatty acid composition of cell membranes.

The percentage of lipid globules is based on volume of total lipid. The mode diameter relates to the diameter which is the most present based on volume of total lipid, or the peak value in a graphic representation, having on the X-as the diameter and on the Y-as the volume (%).

The volume of the lipid globule and its size distribution can suitably be determined using a particle size analyzer such as a Mastersizer (Malvern Instruments, Malvern, UK), for example by the method described in Michalski et al, 2001, Lait 81: 787-796.

The core preferably comprises at least 90 wt. % triglycerides and more preferably essentially consists of triglycerides.

The lipid globules in the nutritional composition according to the present invention have a volume-weighted mode diameter above 1.0 µm, preferably above 3.0 µm, more preferably 4.0 µm or above, preferably between 1.0 and 10 µm, more preferably between 2.0 and 8.0 µm, even more preferably between 3.0 and 7.0 µm, most preferably between 4.0 µm and 6.0 µm. Alternatively, or preferably in addition, the size distribution is in such a way that at least 45 volume %, preferably at least 55 volume %, even more preferably at least 65 volume %, even more preferably at least 75 volume % of the lipid globules have a diameter between 2 and 12 µm. More preferably at least 45 volume %, preferably at least 55 volume %, even more preferably at least 65 volume %, even more preferably at least 75 volume % of the lipid globules have a diameter between 2 and 10 µm. Even more preferably at least 45 volume %, preferably at least 55 volume %, even more preferably at least 65 volume %, even more preferably at least 75 volume % of the lipid globules have a diameter between 4 and 10 µm. Preferably less than 5 volume % of the lipid globules have a diameter above 12 µm.

Phospholipids According to the present invention the nutritional composition comprises polar lipids, in particular phospholipids. Polar lipids are amphipathic of nature and include glycerophospholipids, sphingomyelin, glycosphingolipids, and/or cholesterol. More in particular, the present nutritional composition comprises phospholipids, which are defined as the sum of glycerophospholipids and sphingomyelin. Phospholipids are preferably present in a coating on the surface of lipid globules. By 'coating' is meant that the outer surface layer lipid globules comprise phospholipids, whereas these phospholipids are virtually absent in the core of the lipid globule. The presence of phospholipids in the diet administered early in life was found to advantageously improve the fatty acid composition of cellular membranes. Preferably a part of the phospholipid is in the coating, preferably more than 50 wt. %, more preferably more than 70 wt. %, even more preferably more than 85 wt. %. A suitable way to determine whether phospholipids are located on the surface of lipid globules is confocal laser scanning microscopy or transmission electron microscopy, see for instance Gallier et al, 2015, Colloids Surf B Biointerfaces 136:329-339.

The present nutritional composition preferably comprises glycerophospholipids. Examples of glycerophospholipids are phosphatidylcholine (PC), phosphatidylserine (PS), phosphatidylethanolamine (PE), phosphatidylinositol (PI) and phosphatidylglycerol (PG). Preferably the present nutritional composition contains PC, PS, PI and/or PE, more preferably at least PC. The present nutritional composition preferably comprises sphingomyelin. Sphingomyelins have a phosphorylcholine or phosphorylethanolamine molecule esterified to the 1-hydroxy group of a ceramide. They are classified as phospholipid as well as sphingolipid, but are not classified as a glycerophospholipid nor as a glycosphingolipid. Preferably the present nutritional composition comprises 0.05 to 10 wt. % sphingomyelin based on total lipid, more preferably 0.1 to 5 wt. %, even more preferably 0.2 to 2 wt. %. Preferably the present nutritional composition comprises at least 5 wt. %, more preferably 5 to 40 wt. % sphingomyelin based on total phospholipid, more preferably 10 to 35 wt. %, even more preferably 15 to 35 wt. %.

The present nutritional composition preferably additionally comprises glycosphingolipids. The term glycosphingolipids as in the present invention particularly refers to glycolipids with an amino alcohol sphingo sine. The sphingo sine backbone is O-linked to a charged headgroup such as ethanolamine, serine or choline backbone. The backbone is also amide linked to a fatty acyl group. Glycosphingolipids are ceramides with one or more sugar residues joined in a beta-glycosidic linkage at the 1-hydroxyl position, and include gangliosides. Preferably the present composition contains gangliosides, more preferably at least one ganglioside selected from the group consisting of GM3 and GD3.

Preferably the phospholipids are derived from milk lipids, more preferably form milk fat globule membrane (MFGM). Preferably the phospholipids are derived from cow's milk lipids, more preferably form cow's MFGM. Preferably the present nutritional composition comprises phospholipids and glycosphingolipids and in a preferred embodiment the weight ratio of phospholipids:glycosphingolipids is from 2:1 to 10:1, more preferably 2:1 to 5:1.

Preferably the present nutritional composition comprises 0.5 to 20 wt. % phospholipids based on total lipid, more preferably 0.5 to 10 wt. %, more preferably 0.75 to 8 wt. %, even more preferably 1.0 to 8 wt. % even more preferably 1.5 to 5 wt. % phospholipids based on total lipid. Preferably the present nutritional composition comprises 0.1 to 10 wt. % glycosphingolipids based on total lipid, more preferably 0.5 to 5 wt. %, even more preferably 2 to 4 wt. %.

The present nutritional composition preferably comprises cholesterol. The present nutritional composition preferably comprises at least 0.005 wt. % cholesterol based on total lipid, more preferably at least 0.02 wt. %, more preferably at least 0.05 wt. %., even more preferably at least 0.1 wt. %. Preferably the amount of cholesterol does not exceed 10 wt. % based on total lipid, more preferably does not exceed 5 wt. %, even more preferably does not exceed 1 wt. % of total lipid.

Preferred sources for providing the phospholipids, glycosphingolipids and/or cholesterol are egg lipids, milk fat, buttermilk fat and butter serum fat (such as beta serum fat). A preferred source for phospholipids, particularly PC, is soy lecithin and/or sunflower lecithin. The present nutritional composition preferably comprises phospholipids derived from mammalian milk. Preferably the present nutritional composition comprises phospholipids and glycosphingolipids derived from milk. Preferably also cholesterol is obtained from milk. Phospholipids derived from milk include phospholipids that are isolated from milk lipid, cream lipid, cream serum lipid, butter serum lipid (beta serum lipid), whey lipid, cheese lipid and/or buttermilk lipid. The buttermilk lipid is typically obtained during the manufacture of buttermilk. The butter serum lipid or beta serum lipid is typically obtained during the manufacture of anhydrous milk fat from butter. Preferably the phospholipids, glycosphingolipids and/or cholesterol are obtained from milk cream. The nutritional composition preferably comprises phospholipids, glycosphingolipids and/or cholesterol from milk of cows, mares, sheep, goats, buffalos, horses and camels. It is most preferred to use a lipid extract isolated from cow's milk. The use of phospholipids from milk fat advantageously comprises the use of milk fat globule membranes, which are more reminiscent to the situation in human milk. The concomitant use of polar lipids in particular phospholipids, derived from domestic animals milk and triglycerides derived from vegetable lipids therefore enables to manufacture coated lipid globules with a coating more similar to human milk, while at the same time providing an optimal fatty acid profile. Suitable commercially available sources for milk polar lipids are BAEF, SM2, SM3 and SM4 powder of Corman, Salibra of Glanbia, and LacProdan MFGM-10 or PL20 from Arla.

Methods for obtaining lipid globules with an increased size and/or coating with phospholipids are for example disclosed in WO 2010/0027258 and WO 2010/0027259.

Lipid in the form of large lipid globules and an enhanced amount of phospholipids improves the fatty acid composition of membranes and improves cognitive performance. Together with an optimal fatty acid composition of the diet and the presence of an enhanced amount of sn-2 palmitic acid, a further synergistic effect on membrane composition was observed.

Nutritional Composition

Digestible Carbohydrates

The nutritional composition preferably comprises digestible carbohydrate. The digestible carbohydrate preferably provides 30 to 80% of the total calories of the composition. Preferably the digestible carbohydrate provides 40 to 60% of the total calories. When in liquid form, e.g. as a ready-to-feed liquid, the composition preferably comprises 3.0 to 30 g digestible carbohydrate per 100 ml, more preferably 6.0 to 20, even more preferably 7.0 to 10.0 g per 100 ml. Based on dry weight the present composition preferably comprises 20 to 80 wt. %, more preferably 40 to 65 wt. % digestible carbohydrates.

Preferred digestible carbohydrate sources are lactose, glucose, sucrose, fructose, galactose, maltose, starch and maltodextrin. Lactose is the main digestible carbohydrate present in human milk. Lactose advantageously has a low glycemic index. The present nutritional composition preferably comprises lactose. The present nutritional composition preferably comprises digestible carbohydrate, wherein at least 35 wt. %, more preferably at least 50 wt. %, more preferably at least 75 wt. %, even more preferably at least 90 wt. %, most preferably at least 95 wt. % of the digestible carbohydrate is lactose. Based on dry weight the present composition preferably comprises at least 25 wt. % lactose, preferably at least 40 wt. %.

Non Digestible Carbohydrates

In one embodiment the present nutritional composition preferably comprises non-digestible oligosaccharides. Preferably the present nutritional composition comprises non-digestible oligosaccharides with a degree of polymerization (DP) between 2 and 250, more preferably 3 and 60. The non-digestible oligosaccharides improve the intestinal microbiota and this via the gut brain barrier advantageously affects the brain.

Preferably the present nutritional composition comprises fructo-oligosaccharides, galacto-oligosaccharides and/or galacturonic acid oligosaccharides, more preferably galacto-oligosaccharides, most preferably transgalacto-oligosaccharides. In a preferred embodiment the composition comprises a mixture of transgalacto-oligosaccharides and fructo-oligosaccharides. Suitable non-digestible oligosaccharides are for example Vivinal® GOS (FrieslandCampina DOMO), Raftilin® HP or Raftilose® (Orafti).

Preferably, the nutritional composition comprises 80 mg to 2 g non-digestible oligosaccharides per 100 ml, more preferably 150 mg to 1.50 g, even more preferably 300 mg to 1 g per 100 ml. Based on dry weight, the nutritional composition preferably comprises 0.25 wt. % to 20 wt. %, more preferably 0.5 wt. % to 10 wt. %, even more preferably 1.5 wt. % to 7.5 wt. %. A lower amount of non-digestible oligosaccharides will be less effective in improving the microbiota, whereas a too high amount will result in side-effects of bloating and abdominal discomfort.

Protein

The present nutritional composition preferably comprises proteins. The protein preferably provides 5 to 15% of the total calories. Preferably the present nutritional composition comprises protein that provides 6 to 12% of the total calories. More preferably protein is present in the nutritional composition below 2.25 gram per 100 kcal, more preferably the nutritional composition comprises between 1.8 and 2.1 g protein per 100 kcal, even more preferably between 1.85 and 2.0 g protein per 100 kcal. A low protein concentration advantageously is closer to human milk as human milk comprises a lower amount of protein based on total calories than cow's milk. The protein concentration in a nutritional composition is determined by the sum of protein, peptides and free amino acids. Based on dry weight the nutritional composition preferably comprises less than 12 wt. % protein, more preferably between 9.6 and 12 wt. %, even more preferably between 10 and 11 wt. %. Based on a ready-to-drink liquid product the nutritional composition preferably comprises less than 1.5 g protein per 100 ml, more preferably between 1.2 and 1.5 g, even more preferably between 1.25 and 1.35 g.

The source of the protein should be selected in such a way that the minimum requirements for essential amino acid content are met and satisfactory growth is ensured. Hence protein sources based on cows' milk proteins such as whey, casein and mixtures thereof and proteins based on soy, potato or pea are preferred. In case whey proteins are used, the protein source is preferably based on acid whey or sweet whey, whey protein isolate or mixtures thereof. Preferably the nutritional composition comprises at least 3 wt. % casein based on dry weight. Preferably the casein is intact and/or non-hydrolyzed. For the present invention protein includes peptides and free amino acids.

Other

The present nutritional composition is preferably particularly suitable for providing the daily nutritional requirements to a human with an age below 36 months, particularly an infant with the age below 24 months, even more preferably an infant with the age below 18 months, most preferably below 12 months of age. Hence, the nutritional composition is for feeding or is used for feeding a human subject. The present nutritional composition preferably comprises lipid and protein and digestible carbohydrate wherein the lipid preferably provides 30 to 60% of total calories, the protein preferably provides 5 to 15 wt. %, of the total calories and the digestible carbohydrate preferably provides 30 to 80% of the total calories. Preferably the present nutritional composition comprises lipid providing 35 to 55% of the total calories, protein providing 6 to 12% of the total calories and digestible carbohydrate providing 40 to 60% of the total calories. In one embodiment, the protein provides 5 to 9% of the total calories.

Preferably the present nutritional composition comprises lipid providing 10 to 50 wt. % based on dry weight, protein providing 9.6 to 12 wt. % based on dry weight and digestible carbohydrate providing 20 to 80 wt. % based on dry weight, and optional 0.25 to 20 wt. % of non-digestible oligosaccharides based on dry weight of the nutritional composition.

The present composition preferably is not human milk. The present nutritional composition is not (raw) cow's or other (raw) mammalian milk. The present nutritional composition preferably comprises vegetable lipids. The composition of the invention preferably comprises other ingredients, such as vitamins, minerals, trace elements and other micronutrients according to international directives for infant formulae.

In one embodiment, the nutritional composition according to the invention or the nutritional composition for use according to the invention is an infant formula, follow on formula or growing up milk.

In order to meet the caloric requirements of the infant, the nutritional composition preferably comprises 50 to 200 kcal/100 ml liquid, more preferably 60 to 90 kcal/100 ml liquid, even more preferably 60 to 75 kcal/100 ml liquid. This caloric density ensures an optimal ratio between water and calorie consumption. The osmolarity of the present nutritional composition is preferably between 150 and 420 mOsmol/l, more preferably 260 to 320 mOsmol/l. The low osmolarity aims to reduce the gastrointestinal stress. Stress can have disadvantageous effects on cognitive development.

Preferably the nutritional composition is in a liquid form, with a viscosity below 35 mPa·s, more preferably below 6 mPa·s as measured in a Brookfield viscometer at 20° C. at a shear rate of 100 s$^{-1}$. In one embodiment, the present composition is a powder. Suitably, the composition is in a powdered form, which can be reconstituted with water or other food grade aqueous liquid, to form a ready-to drink liquid, or in a liquid concentrate form that should be diluted with water to a ready-to-drink liquid. It was found that lipid globules maintained their size and coating when reconstituted.

Application

The present nutritional composition is for administration to a human subject and preferably is administered orally to a human subject.

The inventors surprisingly found that when mice early in life were fed a food composition comprising both large lipid globules with phospholipids and with palmitic acid being enriched in the sn-2 position of the triglycerides, a synergistic effect on brain membrane composition later in life was observed when compared to mice that during infancy and childhood had been fed a food composition having a similar fatty acid composition, but no large lipid globules with phospholipids and/or with no palmitic acid being enriched in the sn-2 position of the triglyceride molecule. A synergistic effect, i.e. an effect exceeding the effect than can be expected based on the factors individually, was observed when compared to the sn-2 palmitic acid or large lipid globules with phospholipids alone. In the control mice, which had been fed a standard infant formula early in life and which had subsequently been exposed to a Western style diet, the fatty acid composition of the brain membranes was significantly different and impaired compared to control mice on rodent chow not exposed to a Western style diet. This effect could be partly prevented with a diet with lipid enriched in sn-2 palmitic acid alone or with large lipid globules with phospholipids alone, but the best and most significant effect was observed with the combination.

The effects observed were in particular on the increased concentration of one or more of brain membrane PUFA, n3 and n6 PUFA, LC-PUFA, n3 and n6 LC-PUFA, DHA and ARA.

In a clinical trial wherein the nutritional composition of the present invention was administered to infants up to 17 weeks of age the membrane composition of the red blood cells (RBC) was analysed and found to be more similar to the membrane RBC of breast fed infants when compared to the RBC of infants that had consumed a standard formula. In one embodiment according to the present invention, the cell membranes are red blood cell membranes. In particular the amount of PUFA had increased and the ratio of n6/n3 PUFA had decreased. In one embodiment according to the present invention, the improvement of the fatty acid composition of red blood cell membranes is one or more selected from increased PUFA and decreased weight ratio of n6/n3 LC-PUFA. In one embodiment according to the present invention, the improvement of cell membranes is selected from the group consisting of increasing membrane fluidity, increasing PUFA, increasing LC-PUFA, increasing n3 PUFA, increasing n3 LC-PUFA, increasing DHA, increasing ARA, decreasing weight ratio of n6/n3 PUFA, decreasing weight ratio of n6/n3 LC PUFA. Preferably the improvement of cell membranes is selected from the group consisting of increasing membrane fluidity, increasing PUFA, increasing LC-PUFA, increasing n3 PUFA, increasing n3 LC-PUFA, increasing DHA and increasing ARA. In one embodiment according to the present invention, the improvement of cell membranes is in brain cell membranes and in one embodiment the improvement in brain cell membranes is selected from the group consisting of increasing membrane fluidity, increasing LC-PUFA, increasing n3 LC-PUFA and increasing DHA, more preferably selected from increasing LC-PUFA and increasing DHA. In one embodiment according to the present invention, the improvement of cell membranes is in red blood cell membranes and in one embodiment the improvement in red blood cell membranes is selected from the group consisting of increasing membrane fluidity, increasing LC-PUFA, increasing n3 LC-PUFA, increasing DHA, decreasing weight ratio of n6/n3 PUFA and decreasing weight ratio of n6/n3 LC PUFA, more preferably selected from increasing LC-PUFA, increasing DHA, decreasing weight ratio of n6/n3 PUFA and decreasing weight ratio of n6/n3 LC PUFA.

Brain growth and development, structurally as well as functionally, is highest during halfway the prenatal period and the first three years of life, and continuous until young adulthood.

During early development, brain growth and functional development are highly sensitive to environmental cues including adequate nutrient supply. The dry weight of the brain is composed of about 60% fat, and the fats from our diet directly affect the structure and composition of the brain cell membranes. The communication between neurons via electrical signalling as well as the constant restructuring of connections between neurons makes the brain the most energy demanding organ of the body, hence its structural requirements are different from the rest of the body. The most important component in neuronal communication, the synapse, consists of phospholipids that are very rich in DHA. DHA serves as building block for cell membrane and synapse formation and neurotransmitter production (signals for communication). The total amount of DHA in the brain increases dramatically during the first months of life, not only due to the growth in organ size and cell number, but also due to an increased incorporation of DHA in the cell membranes. The pace at which DHA is incorporated in the brain continues to be very significant until at least 2 years of age. Because of the benefits for the developing child, it is advantageous to establish the advantageous effect of n3 and n6 (LC-)PUFA incorporation, in particular DHA, in cell membranes early in life. Therefore the present nutritional composition is preferably administered to the human subject during the first 3 years of life. In one embodiment according to the present invention, the nutritional composition is administered to or is for feeding or is used for feeding a human subject with an age between 0 and 36 months. The present composition is advantageously administered to a human of 0-24 months, more preferably to a human of 0-18 months, even more preferably to a human of 0-12 months, most preferably a human of 0-6 months.

Functional Brain Effects

The nutritional composition of the present invention provides similar to human milk, important brain building blocks such as DHA, phospholipids, that have been linked to the development of the brain in early life. These building blocks are now part of a lipid globule structure closer to human milk, and without wishing to be bound by theory, support a more efficient transport to and incorporation in the cell membranes compared to a normal infant formula. In one embodiment according to the present invention, the cell membranes are brain cell membranes.

A direct link between the fatty acid composition of brain membranes and functional brain effects later in life was demonstrated in WO 2011/115476 and WO 2011/115491. A low ratio of n6/n3 PUFA has beneficial effects on brain function. In McCann et al, 2005, Am J Clin Nutr, 82: 281-295 clinical and animal studies on the effect of the brain membrane composition on functional brain effects are reviewed and it is concluded that changes in brain concentrations of DHA are positively associated with changes in cognitive or behavioural performance. Likewise an impaired brain membrane fatty acid composition, such as lower amount of (LC-)PUFA, higher ratio n6/n3 of (LC-)PUFA and/or lower amount of n3(LC-)PUFA, in particular DHA, is associated with brain disorders like of attention deficiency, ADHD, autism, dyslexia, depression, bipolar depression, anxiety, schizophrenia, obsessive compulsive disorder, bulimia, abuse of alcohol or drugs, borderline personality disorder, panic disorder, social phobia, cognitive impairment, dementia, Alzheimer's disease and Parkinson's disease.

In one aspect the present invention concerns a method for i) improving cognitive performance and/or improving cognitive development and/or preventing cognitive impairment, ii) improving behavioural performance and/or improving behavioural development, iii) improving visual acuity, and/or iv) improving fine motor skills by improving the fatty acid composition of brain cell membranes in a human subject, preferably for improving cognitive performance, improving cognitive development and/or preventing cognitive impairment by improving the fatty acid composition of brain cell membranes in a human subject, by administering a nutritional composition comprising lipid in the form of lipid globules to the human subject, wherein a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm or at least 45 vol. % have a diameter of 2-12 μm, and
d. the lipid comprises at least 0.5 wt. % phospholipid based on total lipid and either wherein the nutritional composition is not human milk or wherein the nutritional composition comprises vegetable lipid.

The present method can also be referred to as a non-medical method for i) improving cognitive performance and/or improving cognitive development and/or preventing cognitive impairment, ii) improving behavioural performance and/or improving behavioural development, iii) improving visual acuity, and/or iv) improving fine motor skills by improving the fatty acid composition of brain cell membranes in a human subject, preferably as a non-medical method for improving cognitive performance, improving cognitive development and/or preventing cognitive impairment by improving the fatty acid composition of brain cell membranes in a human subject.

For some jurisdictions, the present invention can also be worded as the use of lipid in the manufacture of a nutritional composition for use in i) improving cognitive performance and/or improving cognitive development and/or preventing cognitive impairment, ii) improving behavioural performance and/or improving behavioural development, iii) improving visual acuity, and/or iv) improving fine motor skills by improving the fatty acid composition of brain cell membranes in a human subject, preferably for use in improving cognitive performance, improving cognitive development and/or preventing cognitive impairment by improving the fatty acid composition of brain cell membranes in a human subject, wherein the lipid in the form of lipid globules, wherein
a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm or at least 45 vol. % have a diameter of 2-12 μm, and
d. the lipid comprises at least 0.5 wt. % phospholipid based on total lipid and either wherein the nutritional composition is not human milk or wherein the nutritional composition comprises vegetable lipid.

For some jurisdictions, the present invention can also be worded as a nutritional composition comprising lipid in the form of lipid globules, wherein
a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm or at least 45 vol. % have a diameter of 2-12 μm, and
d. the lipid comprises at least 0.5 wt. % phospholipid based on total lipid and wherein the nutritional composition is not human milk or wherein the nutritional composition comprises vegetable lipid, for use in i) improving cognitive performance and/or improving cognitive development and/or preventing cognitive impairment, ii) improving behavioural performance and/or improving behavioural development, iii) improving visual acuity, and/or iv) improving fine motor skills by improving the fatty acid composition of brain cell membranes in a human subject, preferably for use in improving cognitive performance, improving cognitive development and/or preventing cognitive impairment by improving the fatty acid composition of brain cell membranes in a human subject.

In one aspect the present invention concerns a method for prevention and/or treatment of a disorder associated with impaired brain membrane fatty acid composition selected from the group consisting of consisting of attention deficiency, ADHD, autism, dyslexia, depression, bipolar depression, anxiety, schizophrenia, obsessive compulsive disorder, bulimia, abuse of alcohol or drugs, borderline personality disorder, panic disorder, social phobia, cognitive impairment, dementia, Alzheimer's disease and Parkinson's disease by improving the fatty acid composition of brain cell membranes in a human subject by administering a nutritional composition comprising lipid in the form of lipid globules to the human subject, wherein
a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm and/or at least 45 vol. % have a diameter of 2-12 μm, and
d. the lipid comprises at least 0.5 wt. % phospholipid based on total lipid, and either wherein the nutritional composition is not human milk or wherein the nutritional composition comprises vegetable lipid.

For some jurisdictions, the present invention can also be worded as the use of lipid in the manufacture of a nutritional composition for prevention and/or treatment of a disorder associated with impaired brain membrane fatty acid composition selected from the group consisting of consisting of attention deficiency, ADHD, autism, dyslexia, depression, bipolar depression, anxiety, schizophrenia, obsessive compulsive disorder, bulimia, abuse of alcohol or drugs, borderline personality disorder, panic disorder, social phobia, cognitive impairment, dementia, Alzheimer's disease and Parkinson's disease by improving the fatty acid composition of brain cell membranes in a human subject, wherein the lipid in the form of lipid globules, wherein
a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm and/or at least 45 vol. % have a diameter of 2-12 μm, and
d. the lipid comprises at least 0.5 wt. % phospholipid based on total lipid, and either wherein the nutritional composition is not human milk or wherein the nutritional composition comprises vegetable lipid.

For some jurisdictions, the present invention can also be worded as a nutritional composition comprising lipid in the form of lipid globules, wherein
a. the lipid contains at least 0.5 wt. % alpha-linolenic acid based on total fatty acids and at least 5 wt. % linoleic acid based on total fatty acids, and
b. the lipid contains at least 10 wt. % palmitic acid based on total fatty acids and at least 15 wt. % of palmitic acid, based on total palmitic acid, is located at the sn-2 position of a triglyceride, and
c. the lipid globules have a mode diameter based on volume of at least 1 μm and/or at least 45 vol. % have a diameter of 2-12 μm, and
d. the lipid comprises at least 0.5 wt. % phospholipid based on total lipid, and wherein the nutritional composition is not human milk or wherein the nutritional composition comprises vegetable lipid, for use in prevention and/or treatment of a disorder associated with impaired brain membrane fatty acid composition selected from the group consisting of consisting of attention deficiency, ADHD, autism, dyslexia, depression, bipolar depression, anxiety, schizophrenia, obsessive compulsive disorder, bulimia, abuse of alcohol or drugs, borderline personality disorder, panic disorder, social phobia, cognitive impairment, dementia, Alzheimer's disease and Parkinson's disease, by improving the fatty acid composition of brain cell membranes in a human subject.

Cognitive performance or cognitive development in the present invention refers preferably to any one selected from the group consisting of memory performance or development (such as short term memory, long term memory, episodic memory), learning capacity, alertness, attention, language development, cognitive flexibility, inhibitory control, executive function and concentration capacity, more preferably memory performance, attention, language development and executive function. Hence in one embodiment according to the present invention the improvement of cognitive performance or improvement of cognitive development is selected from the group consisting of improvement of memory performance or memory development, learning capacity, alertness, attention, language development, cognitive flexibility, inhibitory control, executive function and concentration capacity. In one embodiment according to the present invention the prevention of cognitive impairment is selected from the group consisting of impairment of memory performance or memory development, learning capacity, alertness, attention, language development, cognitive flexibility, inhibitory control, executive function and concentration capacity.

A suitable way to assess improved cognitive effects in young children is the NIH Toolbox Early Childhood Cognition Battery (NIH 2012, Mungas, et al. 2013 Monogr Soc Res Child Dev 78:103-118). This battery, recommended for ages 3-6 years, consists of four tasks: the Dimension Change Card Sort (DCCS), Flanker, Picture Sequence Memory, and Picture Vocabulary measures, which assess attention, memory, language and executive function. DCCS is a measure of cognitive flexibility. The Flanker task measures both a participant's attention and inhibitory control. The Picture Sequence Memory Test is a measure developed for the assessment of episodic memory.

Also in younger children and infants development can be assessed, e.g. by the Bayley Scales of Infant and Toddler Development (Bayley-III). It includes the Cognitive Scale, the Language Scale, and the Motor Scale. There are two additional Bayley-II Scales which are dependent on parental report, including the Social-Emotional scale, and the Adaptive Behavior scale. The Bayley-III Cognitive and Language scales are good predictors of preschool mental test performance.

Behavioural performance includes social behaviour, anxiety behaviour and includes social interest and social recognition. Preferably the behavioural performance is social performance and/or anxiety behaviour, more preferably social performance, even more preferably social interest and/or social recognition.

Later in Life

With the animal model employed it was found that beneficial effects of early life diet had long lasting effects extending to later in life, after consumption of the diet had stopped. The present invention is preferably considered to be of benefit at the age above 36 months. In one embodiment the present invention is for achieving improvement of fatty acid composition of cell membranes, preferably of brain cell membranes and/or achieving improvement of cognitive performance, improvement of cognitive development and/or prevention of cognitive impairment, improvement of behavioural development, improvement of behavioural performance, improvement of visual acuity, improvement of fine motor skills, preventing a disorder associated with impaired brain membrane fatty acid composition, when said human subject has an age above 36 months, preferably when said human subject has an age above 5 years, particularly above 11 years, more particularly above 18 years. In one embodiment the present method or the present nutritional composition is for feeding a human subject with an age between 0 and 36 months and for achieving the above improvements and/or prevention when said human subject has an age above 36 months, preferably when said human subject has an age above 5 years, particularly above 11 years, more particularly above 18 years.

Preferably the improvement of fatty acid composition of cell membranes, preferably of brain cell membranes and/or the improvement of cognitive development and/or improvement of cognitive performance and/or prevention of cognitive impairment is extending beyond the time the nutritional composition of the present invention is administered. In one embodiment the present invention is for achieving improvement of fatty acid composition of cell membranes, preferably of brain cell membranes and/or achieving improvement of cognitive development and/or improvement of cognitive performance and/or prevention of cognitive impairment and/or improvement of behavioural development and/or improvement of behavioural performance and/or improvement of visual acuity and/or improvement of fine motor skills and/or preventing a disorder associated with impaired brain membrane fatty acid composition, later in life, preferably at least 1 year after administration of the nutritional composition has stopped, preferably at least 2 years, more preferably at least 3 years, after administration of the nutritional composition has stopped.

In one embodiment, the above improvements and/or prevention later in life are achieved when the human subject is exposed to or raised in an obesogenic environment and/or consumes after infancy a Western style diet that is high in fat and is high in saturated fatty acids, with the fat providing more than 35% of the total calories of the diet, and with the saturated fatty acids providing more than 10% of the total calories of the diet. In a preferred embodiment the Western style diet comprises fat providing between 35 and 45% of the total calories of the diet and comprises saturated fatty acids providing between 10 and 20% of the total calories of the diet.

Although the nutritional composition is in particular suitable for infants, because of the long term effects and the enhanced plasticity of the brain during infancy, the nutritional composition is also suitable for other human subjects.

Obesogenic Environment

Preferably the nutritional composition according to the present invention is administered to human subjects, more preferably human subjects of 0 to 36 months of age, even more preferably infants that are exposed to or raised in an obesogenic environment. In the animal experiment employed, after the early life nutritional intervention, the animals were exposed to a Western style diet, which is indicative for a mild obesogenic environment exposure (such as current diet style/habits in modern Western Society), and found that such a diet adversely affects the brain membrane fatty acid composition. By using an early life diet of the present invention such an adverse effect could be prevented. The term obesogenic environment refers to an environment that promotes gaining weight and to an environment that is not conducive to weight loss within the home or workplace (Swinburn, et al., 1999, Pev Medicine 29:563-570). In other words, the obesogenic environment refers to an environment that promotes, induces, helps, or contributes to, obesity. Factors that contribute are urbanization, often accompanied by a reduction in physical activity, and easy access to food. There is evidence that the food environment in the obesogenic environment not only leads to increased incidence of obesity, but also to the development of cognitive impairment and/or dementia, in particular cognitive impairment on learning and memory functions, more in particular learning and memory functions dependent on the integrity of the hippocampus. Therefore in one embodiment according to the present invention, the prevention of cognitive impairment is cognitive impairment induced by a Western style diet that is high in fat and is high in saturated fatty acids, with the fat providing more than 35% of the total calories of the diet, and with the saturated fatty acids providing more than 10% of the total calories of the diet. More in particular the prevention of cognitive impairment is cognitive impairment induced by a Western style diet that is characterised as comprising fat providing between 35 and 45% of the total calories of the diet and comprising saturated fatty acids providing between 10 and 20% of the total calories of the diet.

In one embodiment, the present invention relates to a method for preventing cognitive impairment induced by a Western style diet that is high in fat and is high in saturated fatty acids, with the fat providing more than 35% of the total calories of the diet, and with the saturated fatty acids providing more than 10% of the total calories of the diet, in a human subject by administering a nutritional composition comprising lipid in the form of lipid globules to the human subject, wherein a. the lipid contains at least 0.5 wt. % alpha-linolenic acid based on total fatty acids and at least 5 wt. % linoleic acid based on total fatty acids, and b. the lipid contains at least 10 wt. % palmitic acid based on total fatty acids and at least 15 wt. % of palmitic acid, based on total palmitic acid, is located at the sn-2 position of a triglyceride, and c. the lipid globules have a mode diameter based on volume of at least 1 μm or at least 45 vol. % have a diameter of 2-12 μm, and d. the lipid comprises at least 0.5 wt. % phospholipid based on total lipid and either wherein the nutritional composition is not human milk or wherein the nutritional composition comprises vegetable lipid.

The present method can also be referred to as a non-medical method for preventing cognitive impairment induced by a Western style diet.

For some jurisdictions, the present invention can also be worded as the use of lipid in the manufacture of a nutritional composition for use in preventing cognitive impairment induced by a Western style diet that is high in fat and is high in saturated fatty acids, with the fat providing more than 35% of the total calories of the diet, and with the saturated fatty acids providing more than 10% of the total calories of the diet in a human subject, wherein the lipid in the form of lipid globules, wherein a. the lipid contains at least 0.5 wt. % alpha-linolenic acid based on total fatty acids and at least 5 wt. % linoleic acid based on total fatty acids, and b. the lipid contains at least 10 wt. % palmitic acid based on total fatty acids and at least 15 wt. % of palmitic acid, based on total palmitic acid, is located at the sn-2 position of a triglyceride, and c. the lipid globules have a mode diameter based on volume of at least 1 μm or at least 45 vol. % have a diameter of 2-12 μm, and d. the lipid comprises at least 0.5 wt. % phospholipid based on total lipid and either wherein the nutritional composition is not human milk or wherein the nutritional composition comprises vegetable lipid.

For some jurisdictions, the present invention can also be worded as a nutritional composition comprising lipid in the form of lipid globules, wherein a. the lipid contains at least 0.5 wt. % alpha-linolenic acid based on total fatty acids and at least 5 wt. % linoleic acid based on total fatty acids, and b. the lipid contains at least 10 wt. % palmitic acid based on total fatty acids and at least 15 wt. % of palmitic acid, based on total palmitic acid, is located at the sn-2 position of a triglyceride, and c. the lipid globules have a mode diameter based on volume of at least 1 μm or at least 45 vol. % have a diameter of 2-12 μm, and d. the lipid comprises at least 0.5 wt. % phospholipid based on total lipid and wherein the nutritional composition is not human milk or wherein the nutritional composition comprises vegetable lipid, for use in preventing cognitive impairment induced by a Western style diet that is high in fat and is high in saturated fatty acids, with the fat providing more than 35% of the total calories of the diet, and with the saturated fatty acids providing more than 10% of the total calories of the diet in a human subject.

In a preferred embodiment the Western style diet comprises fat providing between 35 and 45% of the total calories of the diet and comprises saturated fatty acids providing between 10 and 20% of the total calories of the diet.

For a good understanding it is noted that the saturated fatty acids are part of the fat.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLES

Example 1: Synergistic Effects of Sn-2 Palmitic Acid, and Lipid Globule Design on Brain Fatty Acid Composition Later in Life An experiment was performed wherein the effects of an infant milk formula (IMF) with standard vegetable lipid was compared with IMF wherein the lipid component comprised triglycerides with an increased amount of palmitic acid in the sn-2 position and/or lipid globules enlarged in size and with an increased amount of phospholipids Offspring of C57/BL6 dams were fed on mother's milk only until day 16 after birth. From day 16 onwards, the dams and their offspring were exposed to the experimental diets. Between day 16 and 21 after birth the offspring primarily fed on the experimental diets but were also allowed to drink mother's milk. The offspring were completely fed the experimental diets from day 21 onward. The experimental diets were provided in dough form and exposure to the diets continued until day 42. From day 42 to day 98 all pups were fed the same diet based on AIN-93G diet with an adjusted lipid fraction containing 20 wt. % lipid (17 wt. % lard, 3 wt. % soy oil, 0.1 wt. % cholesterol), representing a mild Western Style Diet (WSD) providing about 40% of the total calories and which contained about 14.5% saturated fatty acids based on total calories so which has an increased level of fat based on total energy and an increased percentage of saturated fatty acids compared to what is considered healthy.

The experimental diets that were used early in life comprised 282 g of experimental infant milk formula (IMF) per kg. The rest of the diet was AIN-93G protein, carbohydrates and fibre. All lipid present in the diet was derived from the IMF. The total amount of lipid was 7 wt. % based on dry weight of the final animal diet.

The experimental IMF used for diet 3 and 4 (NUT and NUT-AMF), which were present in the different diets, were prepared in a similar way as described in example 1B of WO 2010/0027259. The lipid globules of these diets were large. Diet 1 and 2 (CTR and AMF) were prepared with high pressure homogenization, resulting in small lipid globules.

The detailed characteristics of the fat component of the different experimental IMFs used for the different animal diets are shown in Table 1. The amount of DHA was 0.2 wt. %, and the amount of ARA was 0.36 wt. % based on total fatty acids in all 4 experimental diets. The amount of linoleic acid was about 14 wt. %, the amount of ALA was about 2.6 wt. % and the LA/ALA ratio was 5.4 in all 4 diets. Also the rest of the fatty acid composition of the 4 diets was very similar. The ratio of n6/n3 PUFA was about 5 in all diets, and the ratio n6/n3 LC PUFA about 1.5.

For diet 1 (CTR) a mixture of palm oil, low erucic acid rape seed oil, coconut oil, high oleic sunflower oil, sunflower oil, with a small amount of soy lecithin, and LC-PUFA premix was used. The amount of vegetable fat in the final experimental IMF was about 98 wt. % based on total fat, and the amount of milk fat about 1 wt. %.

For diet 2 (AMF) a mix of anhydrous milk fat, coconut oil, low erucic acid rape seed oil, sunflower oil, high oleic acid sunflower oil, with a small amount of soy lecithin and LC-PUFA premix was used. The amount of vegetable fat was about 53 wt. % based on total fat, and the amount of milk fat about 47 wt. %.

Diet 3 (NUT) was similar to diet 1, but additionally comprised buttermilk powder as a source of milk-derived phospholipids. The amount of vegetable fat in the final experimental IMF was about 94 wt. % based on total fat, and the amount of milk fat was about 5 wt. %

Diet 4 of the invention (NUT-AMF) was similar to diet 2, but additionally comprised buttermilk powder as a source of milk derived phospholipids as in diet 3. A little less anhydrous milk fat was added in order to compensate for the milk fat present in butter milk powder. The amount of vegetable fat was about 51 wt. % based on total fat. The amount of milk fat was about 48 wt. %.

The mice were weighed twice a week. At the age of 98 days the male mice were sacrificed and organs including brains were dissected. Of each brain, 1 hemisphere was homogenized (Utra-Turrax T25 basic, IKA, VWR international) in 50 volumes of ice cold deionized water (MiliQ). Subsequently, brain fatty acid (FA) profile was quantified by means of gas chromatographic analysis. 1 ml brain homogenate was extracted according to the procedure of Bligh & Dyer (dichloromethane/methanol extraction). The lipids were converted into methyl esters with concentrated sulfuric acid in methanol. The fatty acid methyl esters (FAME) were extracted from the methanol solution with hexane and analyzed on a gas chromatograph (GC) equipped with a flame ionization detector (FID).

TABLE 1

Characteristics of the fat component of the experimental diets

| | CTR Diet 1 | AMF Diet 2 | NUT Diet 3 | NUT AMF Diet 4 |
|---|---|---|---|---|
| LA | 14 | 14 | 14 | 14 |
| ALA | 2.6 | 2.6 | 2.6 | 2.6 |
| DHA | 0.2 | 0.2 | 0.2 | 0.2 |
| ARA | 0.35 | 0.36 | 0.36 | 0.36 |
| PA* | 18.1 | 18.3 | 18.4 | 17.7 |
| PA at sn-2/total PA | 12 | 35 | 13 | 36 |
| PL** | 0.13 | 0.13 | 1.62 | 1.62 |
| Milk derived PL** | 0 | 0 | 1.49 | 1.49 |
| Size*** | 0.5 | 0.46 | 3.6 | 5.6 |
| 2-12 μm %# | <10 wt. % | <10% | 60 | >45% |

*wt. % based on total fatty acids
**wt. % based on total lipid
*** mode diameter in μm based on volume.
Volume based percentage of lipid globules having a diameter between 2 and 12 μm Results:

At day 98, the FA profile of the brains was determined. Table 2 shows the general FA profile of the brains (PUFA, LCPUFA, n3, n6, n3 LC-PUFA, n6 LC-PUFA) and the profile of the most relevant specific LC-PUFA's (DHA, ARA).

As can be deduced from table 2 the FA composition of the brain of mice that had been consuming control formula early in life and subsequently been exposed to a WSD diet was significantly different from that of the control reference (CTR ref) group, with PUFA, LC-PUFA, n3 PUFA, n3 LC PUFA, DHA, n6 PUFA, n6 LC PUFA and ARA being lower in the CTR WSD group. A diet with large lipid globules and phospholipids, or with anhydrous milk fat both ameliorated the effects and increased PUFA, LC-PUFA, n3 PUFA, n3 LC PUFA, DHA, n6 PUFA, n6 LC PUFA and ARA towards the levels observed in the control mice. However, the highest effects were observed in the experimental diets with both anhydrous milk fat and large lipid globules with phospholipids. These effects were statistically most significant.

TABLE 2

Effect of early life nutritional intervention on later in life brain membrane composition after exposure to Western style diet (in wt. % based on total lipid)

| Fatty acid wt. %/total FA | CTR ref | CTR WSD | AMF | NUT | NUT AMF |
|---|---|---|---|---|---|
| PUFA | 29.23 | 28.78** | 29.05 | 28.82 | 29.34# |
| LC PUFA | 28.27 | 27.81** | 28.10 | 27.86 | 28.43# |
| n3-PUFA | 15.84 | 15.58* | 15.73 | 15.64 | 15.91# |
| n3 LC-PUFA | 15.36 | 15.09* | 15.27 | 15.24 | 15.46# |
| DHA | 14.96 | 14.67* | 14.86 | 14.75 | 15.05# |
| n6 PUFA | 13.33 | 13.14** | 13.25 | 13.12 | 13.38# |
| n6 LC-PUFA | 12.85 | 12.66** | 12.77 | 12.64 | 12.89# |
| ARA | 9.25 | 9.07** | 9.19 | 9.04 | 9.26# |

*p < 0.1 compared to CTR ref,
**p < 0.05 compared to CTR REF.
p < 0.05 compared to CTRL WSD In Table 3 the synergism of the anhydrous milk fat (AMF), being enriched in palmitic acid at the sn-2 position, and the large lipid globules with phospholipids is demonstrated. Here the Brain FA composition of the CTR WSD diet 1 group was set at zero and the difference of the fatty acid composition is given for the different diet groups. An increase is observed for diet 2 with AMF and diet 3 with large lipid globules and phospholipids (NUT) for all FA shown. The additive effect of these two diets is calculated in the last column (Δ theory AMF+NUT). However, surprisingly the effect of the diet that both contained AMF and large lipid globules (AMF+NUT) shows much higher increases for all FA shown, than can be expected based on the additive effect alone.

These data are indicative for an improved effect of the fatty acid composition of cell membranes, in particular brain membranes. These results are indicative for an improved functional brain performance or development, in particular cognitive performance or development. These effects are particular indicative for an effect later in life, extending beyond the period wherein the early in life diet has been administered.

TABLE 3

Difference between fatty acid composition (in wt. % based on total fatty acids) of brain membranes later in life after exposure to Western style diet, when compared to the control diet CTR WSD.

| ΔFatty acid %/total FA | AMF* Diet 2 | NUT* | NUT AMF* | theory (AMF + NUT) |
|---|---|---|---|---|
| PUFA | 0.26 | 0.04 | 0.56 | 0.30 |
| LC-PUFA | 0.29 | 0.05 | 0.62 | 0.34 |
| n3-PUFA | 0.15 | 0.06 | 0.33 | 0.21 |
| n3 LC-PUFA | 0.18 | 0.07 | 0.37 | 0.25 |
| DHA | 0.19 | 0.08 | 0.39 | 0.11 |
| n6 PUFA | 0.11 | −0.02 | 0.24 | 0.09 |
| n6 LC-PUFA | 0.11 | −0.02 | 0.23 | 0.10 |
| ARA | 0.12 | −0.02 | 0.19 | 0.10 |

*The value of the CTR-WSD was set at 0.

Example 2: Effect of an IMF with Increased Sn2 Palmitic Acid, Phospholipids and Large Lipid Globule in the Fatty Acid Composition of Red Blood Cell (RBC) Membranes In a randomized, multi-country, double-blinded, prospective, controlled clinical trial, infants were enrolled up to 35 days of age and assigned to receive one of two formulas until 17 weeks of age: 1) Control: a standard infant milk formula with a lipid component as in diet 1 of example 1, or 2) Experimental: an infant formula with larger phospholipid-coated lipid globules and milk fat as in diet 4 of example 1. Apart from their lipid quality, the formula compositions were identical (66 kcal, 1.3 g protein, 7.3 g carbohydrates and 3.4 g fat per 100 ml). A group of exclusively breastfed infants until at least 13 weeks of age served as reference. A blood sample was taken in a subgroup when the infants were 3 months of age. In the experimental subgroup 31 infants were enrolled, in the control subgroup 25 infants and in the breastfed reference subgroup 25 infants.

Results:

The PUFA concentration in the RBC membranes was highest in the experimental group (experimental: mean 31.79%, median 33.7% based on total fatty acids), when compared with the control group (mean 31.57% and median 32.5% based on total fatty acids), the difference between the median values having a p=0.05 as determined by Mann-Whitney test).

There was a trend that the n3 PUFA and n3 LC-PUFA were higher in the experimental group, and closer to the breast-fed group, than the control group. There was a trend that the n6/n3 PUFA ratio was lower in the experimental group, and more close to the breast-fed group. The strongest effect was observed for the n6/n3 LC-PUFA ratio with a mean of 3.00 and median of 2.9 in the experimental group, and a mean of 3.36 and median of 3.1 in the control group, and a mean of 2.74 and median of 2.7 in the breast fed reference group, hence the n6/n3 LC-PUFA ratio in the experimental group was more close to the breast-fed group. The difference in median between the experimental and control group had a p of 0.03 as determined by Mann-Whitney test.

These results are indicative for an improved fatty acid composition of cell membranes, in particular RBC membranes, when consuming a diet of the present invention, in particular in infants.

The invention claimed is:

1. A method for improving the fatty acid composition of cell membranes in a human subject, the method comprising administering to the subject a nutritional composition comprising lipid in the form of lipid globules, wherein the lipid comprises
   (i) at least 0.5 wt. % alpha-linolenic acid based on total fatty acids,
   (ii) at least 5 wt. % linoleic acid based on total fatty acids,
   (iii) at least 10 wt. % palmitic acid based on total fatty acids, wherein at least 25 wt. % of the palmitic acid, based on total palmitic acid, is located at the sn-2 position of a triglyceride, and
   (iv) at least 1.5 wt. % phospholipid based on total lipid, wherein a part of the phospholipid is in the coating of the lipid globule,
   wherein the lipid globules have a mode diameter based on volume of at least 1 μm and/or at least 45 vol. % have a diameter of 2-12 μm, wherein the nutritional composition comprises vegetable lipid or is not human milk, and wherein the cell membranes are brain cell membranes or red blood cell membranes.

2. The method according to claim 1, wherein the improvement of cell membranes is selected from the group consisting of increasing membrane fluidity, increasing PUFA, increasing LC-PUFA, increasing n3 PUFA, increasing n3 LC-PUFA, increasing DHA, increasing ARA, decreasing weight ratio of n6/n3 PUFA, and decreasing weight ratio of n6/n3 LC PUFA.

3. A method for (i) improving cognitive performance and/or improving cognitive development, (ii) improving behavioural performance and/or improving behavioural development, (iii) improving visual acuity, and/or (iv) improving fine motor skills by improving the fatty acid composition of brain cell membranes in a human subject, the method comprising administering to the subject a nutritional composition comprising lipid in the form of lipid globules, wherein the lipid comprises
   (i) at least 0.5 wt. % alpha-linolenic acid based on total fatty acids,
   (ii) at least 5 wt. % linoleic acid based on total fatty acids,
   (iii) at least 10 wt. % palmitic acid based on total fatty acids, wherein at least 25 wt. % of the palmitic acid, based on total palmitic acid, is located at the sn-2 position of a triglyceride, and
   (iv) at least 1.5 wt. % phospholipid based on total lipid, wherein a part of the phospholipid is in the coating of the lipid globule,
   wherein the lipid globules have a mode diameter based on volume of at least 1 μm and/or at least 45 vol. % have a diameter of 2-12 μm, and wherein the nutritional composition comprises vegetable lipid or is not human milk.

4. The method according to claim 3, for improving cognitive performance and/or improving cognitive development.

5. The method according to claim 4, wherein the improvement of cognitive performance or improvement of cognitive development is selected from the group consisting of improvement of memory performance or memory development, learning capacity, alertness, attention, language development, cognitive flexibility, inhibitory control, executive function and concentration capacity.

6. The method according to claim 3, wherein the phospholipids comprise at least 5 wt. % sphingomyelin based on total phospholipids.

7. The method according to claim 3, wherein the nutritional composition comprises at least 0.1 wt. % of docosahexaenoic acid based on total fatty acids.

8. The method according to claim 3, wherein the human subject is an infant or young child with an age of 0 to 36 months.

9. The method according to claim 3, wherein the improvement is achieved later in life.

10. The method according to claim 9, wherein the improvement is achieved at least one year after the administration of the nutritional composition has stopped.

11. The method according to claim 3, wherein the improvement is achieved when the human subject has an age above 36 months.

12. The method according to claim 3, wherein the human subject is exposed to or raised in an obesogenic environment and/or consumes after infancy a Western style diet that is high in fat and is high in saturated fatty acids, with the fat providing more than 35% of the total calories of the diet, and with the saturated fatty acids providing more than 10% of the total calories of the diet.

13. The method according to claim 3, wherein the composition comprises palmitic acid in an amount of 15 to 30 wt. % based on total fatty acids and 25 to 40 wt. % of the palmitic acid is in the sn-2 position in a triglyceride.

14. The method according to claim 3, wherein the nutritional composition comprises total lipid in an amount of 10 to 50 wt. % based on dry weight, protein in an amount of 9.6 to 12 wt. % based on dry weight and digestible carbohydrate in an amount of 20 to 80 wt. % based on dry weight.

15. The method according to claim 14, wherein the composition further comprises 0.25 to 20 wt. % of non-digestible oligosaccharides based on dry weight of the nutritional composition.

16. The method according to claim 3, wherein the nutritional composition is an infant formula or follow on formula or young child formula.

* * * * *